United States Patent [19]

Herrmann et al.

[11] Patent Number: 5,556,746
[45] Date of Patent: Sep. 17, 1996

[54] ANTIBODIES SPECIFIC FOR THE GROUP ANTIGEN OF ASTROVIRUSES

[75] Inventors: John E. Herrmann, Northboro; Neil R. Blacklow, Weston, both of Mass.

[73] Assignee: University of Massachusetts Medical Center, Worcester, Mass.

[21] Appl. No.: 259,405

[22] Filed: Jun. 14, 1994

Related U.S. Application Data

[63] Continuation of Ser. No. 375,982, Jul. 5, 1989, abandoned.

[51] Int. Cl.$^6$ .............................. C12Q 1/70; C12N 15/06; C12N 5/12; C07K 16/14
[52] U.S. Cl. ...................... 435/5; 435/172.2; 435/240.27; 435/975; 436/548; 530/388.3
[58] Field of Search .................................. 435/5, 7.9, 7.92, 435/7.93, 7.94, 7.95, 975, 172.2, 240.27; 530/388.3; 436/547, 548, 531, 518, 808

[56] References Cited

U.S. PATENT DOCUMENTS 4,814,268  3/1989  Kreider et al. .......................... 435/239

OTHER PUBLICATIONS

Antibodies A Laboratory Manual, Harlow and Lane, Cold Spring Harbor Laboratory, pp. 210–213 (1988).
Abstracts of the Annual Meeting of the American Society for Microbiology "C–117–Hudson et al. Propagation of the Marin County Strain of Astrovirus and Its Detection by Monoclonal Antibody" p. 351 (May 1988).
Sevier et al "Monoclonal Anibodies in Clinical Immunology" clin Chem 27(11) pp. 1797–1806 (1981).

Kurtz, J. B. and T. W. Lee, *Lancet*, p. 1405 (Dec. 15, 1984).

Hudson, R. W., et al., Abstracts of the 1987 ICAAC, p. 99 #18.

Herrmann, J. E., et al., *J. Infect. Dis.*, 158: 182–185 (1988).

Herrmann, J. E., et al., Abstracts of the 1989 ICAAC, p. 176 #454.

*Primary Examiner*—Toni R. Scheiner
*Assistant Examiner*—Donna C. Wortman
*Attorney, Agent, or Firm*—Hamilton, Brook, Smith & Reynolds, P.C.

[57] ABSTRACT

The present invention is based upon the discovery of a group antigen common to various types of astroviruses and the production of polyclonal and monoclonal antibodies reactive with this group antigen. The present invention encompasses the polyclonal antibodies, monoclonal antibodies, hybridoma cell lines which produce these monoclonal antibodies, and methods of using the monoclonal antibodies for diagnosing and treating gastroenteritis.

11 Claims, No Drawings

ANTIBODIES SPECIFIC FOR THE GROUP ANTIGEN OF ASTROVIRUSES

This application is a continuation of application Ser. No. 07/375,982 filed Jul. 5, 1989, now abandoned.

BACKGROUND OF THE INVENTION

Astroviruses were first visualized by electron microscopy (EM) of specimens from infants with gastroenteritis (Madeley et al., Lancet 2:451–452 (1975). Since that time, there have been several reports of infantile gastroenteritis due to astroviruses (Kurtz et al., J. Clin. Pathol. 30:94814 952 (1977); Madeley et al., J. Hyg. (Lond) 78:261–273 (1977); Ashley et al., J. Clin. Pathol. 31:939–943 (1978); Konno et al., J. Med. Virol. 9:11–17 (1982)). Infections in adults have also been reported and there have been suggestions that these viruses have been involved in food and water-borne outbreaks of gastroenteritis (Kurtz et al., Ciba Found. Symp. 128:92–107 (1987).

In most studies, EM of stool samples has been the sole means of establishing the diagnosis of astrovirus infection. Kurtz and co-workers (Kurtz et al., J. Gen. Virol. 57:421–421 (1981) reported serial cultivation of the virus and later determined that five astrovirus types could be distinguished by serological methods (Kurtz et al., Lancet 2:1405 (1984).

The true incidence of astrovirus infection has been difficult to establish because of the lack of convenient and efficacious identification and detection techniques. Diagnostic techniques using EM for observing the presence or absence of an astrovirus in a biological sample are labor-intensive and are not always reliable due to the risk of human error. According to Kurtz and co-workers, (Kurtz et al., Lancet 2:1405 (1984) astrovirus antisera is type specific. Therefore, an antiserum against one strain of astrovirus may not be capable of detecting a different strain of astrovirus.

SUMMARY OF THE INVENTION

The present invention is based upon the discovery of a group antigen common to various types of astroviruses and the production of monoclonal and polyclonal antibodies reactive with this group antigen. The preferred antibody is the monoclonal antibody. The present invention encompasses the monoclonal and polyclonal antibodies, hybridoma cell lines which produce the monoclonal antibodies, and methods of using the monoclonal antibodies.

The monoclonal antibodies can be used in immunoassays for detecting the presence or absence of an astrovirus in a sample or for quantitating the amount of astrovirus in a biological sample, such as stool, urine, or blood. In such assays, the biological sample is contacted with a labelled monoclonal antibody reactive with a group antigen of astroviruses under conditions which allow the labelled monoclonal antibody to bind to the group antigen, if astrovirus is present in the sample, and the presence or absence or amount of the bound labelled monoclonal antibody is detected as an indication of the presence or absence of an astrovirus in the biological sample. The immunoassays can be used for diagnosing whether an individual is afflicted with gastroenteritis.

The monoclonal antibodies of the present invention can also be used in methods of treating gastroenteritis in an individual comprising administering to the individual a therapeutically effective amount of a monoclonal antibody reactive with the group antigen of astroviruses. The monoclonal antibody can also be administered as a composition comprising the monoclonal antibody and a pharmaceutically acceptable carrier.

The monoclonal antibodies, reacting broadly with human astroviruses, can be used to rapidly diagnose astrovirus infection and for determining the importance of these viruses as agents of viral gastroenteritis. Their capability of reacting with the different types of astrovirus is advantageous because a biological sample can be tested for the different types of astroviruses simultaneously using one test or kit.

DETAILED DESCRIPTION

The monoclonal and polyclonal antibodies of this invention react with a group antigen or a portion thereof of astroviruses. The term antibody is intended to include whole antibodies and fragments thereof wherein the fragments are those fragments sufficient for the antibody to bind to the antigen. A group antigen is an antigen common to a substantial amount of the members in a group, preferably common to all members of a group. The group antigen includes the isolated whole antigen, as it appears in nature, or a portion thereof and a synthetic polypeptide having the same or similar amino acid sequence as the group antigen, as it appears in nature, or a portion thereof. A portion thereof is defined as a subunit of the antigen which will bind with polyclonal and monoclonal antibodies specific for the group antigen. The group antigen of astroviruses is present in the five types of known astrovirus (1, 2, 3, 4, and 5). The group antigen of astroviruses can be isolated from the biological samples using conventional protein separation techniques, e.g., gel electrophoresis and affinity chromatography. (Ausebel et al Current Protocols in Molecular Biology, (1987)).

Upon isolation, the group antigen can be sequenced using conventional genetic engineering techniques. A synthetic polypeptide can be produced having the same or similar amino acid sequence as the group antigen. A similar amino acid sequence is defined as an amino acid sequence having substantial homology or being capable of performing the same biological function. The group antigen can be used in vaccines against gastroenteritis.

The polyclonal antibodies of the present invention or antisera reactive with the group antigen of astroviruses can be produced by immunizing an animal with astrovirus (e.g., virus extracted from cells or crude cell extracts) under conditions whereby polyclonal antibodies are produced. Blood is collected from the animal and the serum is separated from the whole blood products thereby obtaining the polyclonal antisera. B Unlike serotype-specific antibodies, monoclonal antibodies of this invention can be used to detect the various types of astroviruses and, therefore, are useful in the detection or diagnosis of gastroenteritis. The anti-astrovirus antibodies are produced by antibody-producing cell lines. The anti-astrovirus antibody-producing cell lines may be hybridoma cell lines commonly known as hybridomas. The hybrid cells are formed from the fusion of an anti-astrovirus antibody-producing cell and an immortalizing cell line, that is, a cell line which imparts long term tissue culture stability on the hybrid cell. In the formation of the hybrid cell lines, the first fusion partner—the anti-astrovirus antibody-producing cells—may be a spleen cell of an animal immunized against astroviruses. The second fusion partner—the immortal cell—may be a lymphoblastoid cell or a plasmacytoma cell such as a myeloma cell, itself an antibody producing cell but also malignant.

Murine hybridomas which produce monoclonal anti-astrovirus antibodies are formed by the fusion of mouse myeloma cells and spleen cells from mice immunized against astroviruses. For example, the immunogen can be the astroviruses or crude cell extracts containing the same. To immunize the mice, a variety of different immunization protocols may be followed. Fusions are accomplished by standard procedures. Kohler and Milstein, (1975) *Nature (London)* 256, 495–497; Kennet, R., (1980) in *Monoclonal Antibodies* (Kennet et al., Eds. pp 365–367, Plenum Press, New York).

The hybridomas are screened for production of antibody reactive with astroviruses. Those which secrete reactive antibodies can be cloned.

Human hybridomas which produce monoclonal anti-astrovirus antibodies are formed from the fusion of spleen cells from an individual immunized against astroviruses and a human lymphoblastoid cell line. The fusion and screening techniques are essentially the same as those used on the production and selection of murine anti-astrovirus generating hybridomas.

Also mouse and human hybridomas which produce human monoclonal anti-astrovirus antibodies can be formed from the fusion of a human antibody producing cell line in a murine plasmacytoma cell. Indeed, the mouse plasmacytoma cell can used as a fusion partner for other mammalian antibody-producing cells to form hybridomas which secrete anti-astrovirus antibody of the particular mammal.

The monoclonal anti-astrovirus antibodies can be produced in large quantities by injecting anti-astrovirus antibody-producing hybridomas into the peritoneal cavity of the mice and, after an appropriate time, harvesting the ascites fluid which contains very high titer of homogeneous antibody and isolating the monoclonal anti-astrovirus antibodies therefrom. Alternatively, the antibodies may be produced by culturing anti-astrovirus producing cells in vitro and isolating secreted monoclonal anti-astrovirus antibodies from the cell culture media.

The monoclonal anti-astrovirus antibodies of this invention can be used for therapeutic purposes such as for the treatment of gastroenteritis. When used as a therapeutic agent, the monoclonal antibody can be administered alone or in combination with a pharmaceutically acceptable carrier. A therapeutically effective amount of a monoclonal antibody is administered to an individual believed to be afflicted with gastroenteritis. A therapeutically effective amount is that amount which is necessary to significantly reduce or eliminate the symptoms associated with gastroenteritis. The therapeutically effective amount of antibody administered to an individual will be determined on an individual basis and will be based, at least in part, on consideration of the individual's size, the severity of symptoms to be treated, the result sought, the specific antibody, etc. Thus, therapeutic effective amount can be determined by one of ordinary skill in the art employing such factors and using no more than routine experimentation.

The antibodies can be administered orally, by subcutaneous or other injection, intravenously, intramuscularly, parenternally, transdermally or rectally. The form in which the antibody is administered (e.g. capsule, solution, emulsion) will depend on the route by which it is administered.

Because of the broad reactivity of the monoclonal anti-astrovirus antibody with the different types of astroviruses, the antibodies are useful in a variety of procedures for detecting the presence or absence of astroviruses in a sample or the amount of astroviruses in a sample. For this purpose the anti-astrovirus antibodies may be used in a number of different immunoassays for astroviruses. These include radioimmunoassays, enzyme linked immunoabsorbent assays (ELISA), immunofluorescent detection methods, sandwich assays, agglutination and precipitation assays, of the conventional types.

For many of these assays an immunoabsorbent is formed by attaching an anti-astrovirus antibody to a solid phase. In a competitive immunoassay (e.g., radioimmunoassay) for astrovirus, a sample of the biologic fluid to be assayed is contacted with the immunoabsorbent. The mixture is incubated after which a predetermined amount of labelled group antigen is added. After further incubation, the immunoabsorbent with the bound group antigen (that is, the group antigen anti-astrovirus complex) is separated from the free group antigen and the activity of the label in the bound or free group antigen fraction is measured in order to determine the amount of astrovirus in the sample. In such assays, the label may be a radioisotope (radioimmunoassay), an enzyme, or a fluorescent compound.

In an ELISA, the biological fluid is contacted with the solid phase such that the antigens from said fluid are absorbed onto the solid phase. The anti-astrovirus antibody is placed in contact with the immunoabsorbent under conditions (e.g., incubation) whereby the antibody is allowed to bind to the appropriate antigen. Subsequently, a second labelled antibody directed towards the anti-astrovirus antibody is added and incubated under conditions which allow binding to occur. The substrate for the enzyme is added and the absorbance of the solution is measured using a spectrophotometer. Alternatively, in an ELISA the anti-astrovirus antibody may be directly labelled with an enzyme.

Fluorescent microscopy can also be used to observe the presence or absence or quantity of anti-astrovirus antibodies in a sample. In one form, the anti-astrovirus antibodies themselves are labelled with the fluorescent compound such as fluorescein, and then brought into contact with a biological sample. In an alternate format, unlabelled anti-astrovirus antibodies are contacted with the biological sample and then a second fluorescently labelled antibody directed against the anti-astrovirus antibody is added. In either format, binding of the anti-astrovirus antibodies to the biological fluid can be monitored under a microscope.

The preferred immunoassay of the present invention is the sandwich immunoassay. The sandwich immunoassay can be used in a variety of formats using either monoclonal antibodies on both sides, polyclonal antibodies on both sides, or a monoclonal antibody on one side and a polyclonal antibody on the other side. Further, the sandwich assay can be a forward, reverse or simultaneous sandwich assay as described in U.S. Pat. No. 4,376,110 issued Mar. 8, 1983, the contents of which are hereby incorporated by reference. The label which is detected as a measure of the astrovirus in the sample can be on either the bound antibody or the free antibody.

In one format, an immuno-absorbent is formed by attaching an anti-astrovirus antibody to a solid phase. Biological fluid is contacted with the immunoabsorbent under conditions (e.g., incubation) which allow binding of the antibodies to the astrovirus antigens to occur. Subsequently, a second labelled monoclonal antibody reactive with the group antigen of astroviruses is added to the mixture under conditions (e.g., incubation) which allow binding to occur between the second antibody and the group antigen. The label is measured as an indication of the presence or absence or the quantity of astrovirus in the sample.

Another format for a sandwich assay uses both a monoclonal antibody and a polyclonal antibody. The monoclonal antibody can be used as either capture antibody or the detector antibody. When used as the capture antibody, an immunoabsorbent is formed by attaching the monoclonal antibody to a solid phase. The biological fluid to be tested is contacted with the immunoabsorbent under conditions (e.g., incubation) which allow binding of the antibody to the antigen to occur. Subsequently, labelled polyclonal antibodies are added to the biological fluid under conditions (i.e., incubation) which allow binding to occur. The label of the bound antibody or the free antibody can be measured as an indication of the presence or absence of astrovirus in the sample. The above sandwich assays can be modified such that they become indirect sandwich assay wherein the detector polyclonal antibody or monoclonal antibody is not labelled and a labelled antibody directed toward the detector polyclonal antibody or monoclonal antibody are added to the reaction mixture under conditions (e.g., incubation) which allow binding of the labelled antibody to the anti-astrovirus antibody to occur.

The above-described immunoassays can be used to quantitate the astrovirus in a sample by establishing a standard curve. A standard curve relating quantity of astrovirus to value indicative of the amount of the particular of the label, (e.g., absorbance) can be established using standards having known astrovirus content. After preparation of such a curve, the quantity of astrovirus in a sample can be determined by extrapolating a quantity of astrovirus from the curve upon obtaining a value indicative of the amount of label (e.g., absorbance).

The assays described above would provide physicians with a quick and reliable method of determining whether an individual is afflicted with gastroenteritis.

Diagnostic kits for performance of the assays described above can include monoclonal anti-astrovirus antibody or labelled anti-astrovirus antibody or mixtures of labelled or unlabelled antibody is in a container. The kits can further include a solid phase having a monoclonal astrovirus antibody or polyclonal astrovirus antibodies absorbed thereon.

The invention will now be further illustrated by the following examples.

EXAMPLE 1

Preparation of Anti-Astrovirus Monoclonal Antibodies

Astrovirus types 1–5, which have been cultivated in human embryonic kidney (HEK) cells, LLCMK$_2$ cells, or both, and rabbit hyperimmune sera to the five serotypes have previously been described (Lee et al *J. Gen Virol.* 57:421–424 (1981); Kurtz et al Lancet 2:1405 (1984)). The sources for adenovirus types 2, 40, and 41; human calicivirus; Hawaii virus; and Norwalk virus have been described (Herrmann et al *Arch Virol* 94:259–65 (1987); Herrmann et al *J. Med. Virol* 17:127–33 (1985)). Coxsackievirus types A9 and B2 were obtained from the Research Resources Branch, National Institutes of Health (Bethesda, Md.). Feline calicivirus and rotavirus SA11 were obtained from the ATCC (Rockville, Md.). Stool samples containing Snow Mountain Virus were obtained from R. Glass, Centers for Disease Control (Atlanta). Canine calicivirus and stool samples containing unclassified "small round viruses" were obtained from W. D. Cubitt, Central Middlesex Hospital (London). A stool sample containing Marin County agent was obtained from H. B. Greenberg, Stanford University (Stanford, Calif.).

Cultivation of Virus

The procedure for cultivating astroviruses was that described previously by Lee et al (*J. Gen. Virol.* 57:421–24 (1981)). Cell-passaged strains of astrovirus types 1–5 were inoculated onto monolayers of human embryonic kidney (HEK) cells or LLCMK$_2$ cells or both and were adsorbed for 1.5 hours at 20°–22° C. on a rocking platform. The diluent for virus was Medium 199 containing antibiotics (penicillin and streptomycin) plus 10 µg of trypsin/mL (Difco 1:250 trypsin; Difco, Detroit). Maintenance medium (same as diluent) was added, and the cells were incubated at 37° C. for two to five days. Cells generally became detached from the surface of the plastic culture flask by two days. For antigenic testing, astrovirus types 1 and 2 were grown in LLCMK$_2$ cells and types 4 and 5 in HEK cells. Viruses were passaged by one cycle of freeze-thawing (–80° C.) and were stored at –80° C.

Hybridoma Production

BALB/c mice (eight-week-old females) were inoculated intraperitoneally (ip) with purified astrovirus type 2 emulsified in an equal volume of Freund's incomplete adjuvant. The virus, grown in LLCMK$_2$ cells and banded in cesium chloride (CsCl), had been dialyzed against 0.01M phosphate buffered saline (PBS)—pH 7.2 before use. The mice were given a second ip inoculation four weeks later. The mice were bled, and the sera were checked for antibody to astrovirus type 2. The mice were given two more ip inoculations four weeks apart. Thirty days after the last ip inoculation, the spleen of one mouse was removed and stimulated in vitro (DuPont in vitro immunization system; DuPont, Wilmington, Del.) with purified astrovirus type 2.

After three days in culture, the stimulated spleen cells were fused to SP 2/0 myeloma cells by using polyethylene glycol (PEG) 1000. Hybrid cells were seeded onto plates, and 24 hours later, a feeder layer of 10$^6$ fresh mouse thymus cells and hypoxanthine-aminopterin-thymidine (HAT) media were used to screen the hybridomas for antibody-producing cells. Hybridomas were screened for antibodies that showed a dual reaction with astrovirus types 2 and 5 by Enzyme Linked Immunoabsorbent Assay (ELISA). Hybridomas that secreted such antibodies were cloned twice by using the limiting dilution technique, and the resulting hybridomas were stored in liquid nitrogen. Ascitic fluids for all clones were prepared in BALB/c mice, as previously described by Herrmann et al (*Arch. Virol.* 94:259–65 (1987).

EXAMPLE 2

Enzyme Linked Immunoabsorbent Assay for Screening Hybridoma Supernatant Fluids, Testing Virus-Specific Reactivity and Screening Stool Samples ELISA tests were used for screening hybridoma supernatant fluids and for testing virus-specific reactivity. For these tests, astroviruses were extracted from infected cells by one freeze-thaw cycle, and 0.05 mL was adsorbed to wells of poly-L-lysine-coated microtiter plates overnight at 4° C., as described for enteroviruses Herrmann et al (*J. Clin. Microbiol.* 10:210–7 (1979)). The plates were washed five times with 0.01M PBS (pH 7.0) containing 0.1% sodium azide. Hybridoma supernatant fluids or rabbit antisera (0.05 mL), diluted in 50% fetal calf serum and 50% 0.1M Tris-HCL buffer (pH 7.2) with 0.15% Tween 20, were added to the wells and incubated for 1 hour at 37° C.; the plates were washed five times. For stools, samples were diluted in 0.01M PBS (pH 7.0) for adsorption to poly-L-lysine-coated plates. Peroxidase-labeled goat antibody to either mouse or rabbit IgG as appropriate (heavy and light chains, 0.05 mL;

(Kirkegaard and Perry Laboratories, Gaithersburg, Md.), at 1 μg/mL in the Tris buffer used above, was added and incubated for 1 hour at 37° C. The plates were washed five times with PBS, soaked for 30 seconds with PBS containing 0.05% Tween 20, and washed again. Substrate for peroxidase (0.1 mL, 0-phenylene-diamine-$H_2O_2$; Abbott Laboratories, North Chicago, Ill.) was added for 10 minutes, and the reaction was stopped with 0.2 mL of 1N $H_2SO_4$. Monoclonal antibodies were also tested by ELISA using plates coated with specific rabbit antisera (plates coated at 1 μg/ml antibody in PBS (pH 7.2) for 18 hours at 20°–22° C.). The remainder of the procedure was as described above. The absorbance of the solution was measured at 490 nm in a plate-reader spectrophotometer. Samples were considered positive for monoclonal antibody to astroviruses in the screening test, or for astrovirus antigen in the virus-specificity tests, if the absorbance value was both ≧0.1 and three or more times the negative control (uninfected cell culture extracts).

EXAMPLE 3

Immunofluoresence (IF)

Infected cells were removed from suspension by centrifugation on glass slides (Cytospin centrifuge; Shandon, Pittsburgh) and fixed with 120° C. acetone for 10 minutes. Antiserum was diluted in 0.01M PBS (pH 7.0) and incubated in a moist chamber for 30 minutes at 37° C. Slides were rinsed for 10 minutes in PBS, and fluorescein-labeled goat antibody to rabbit IgG (Kirkegaard and Perry or Tago, Burlingame, Calif.), at a dilution of 1:20 or 1:40 in PBS, was added and incubated for 30 minutes at 37° C. The slides were rinsed again for 10 minutes in PBS, dipped in distilled water, mounted in phosphate-buffered glycerol, and examined with a fluorescence microscope. The presence of a fluorescent label was an indication of the presence of astrovirus specific antibodies.

EXAMPLE 4

Monoclonal Antibodies

The selected hybridoma, which produced antibodies reactive with both astrovirus types 2 and 5, was designated clone 8E7. Samples of the 8E7 producing hybridoma designated 7F2-6 D4-8E7 were deposited with the American Type Culture Collection, 12301 Parklawn Drive, Rockville, Md. 20852, U.S.A., on Jun. 14, 1995 and were assigned accession number ATCC HB 11945. The antibody isotype was IgG1. The specificity of the antibodies for astroviruses was examined by ELISA tests with representative types of enteric viruses. The results, presented in Table 1, indicate that antibody reactivity did not occur with any of the nonastrovirus enteric viruses under the conditions used for testing. Passive adsorption of viruses to plates with poly-L-lysine, as was done here, is usually satisfactory for cell-cultivated viruses but is probably not as effective for most viral types in stool specimens. All of the stool samples tested, however, had been shown to contain virus by EM and, for Norwalk virus, by immunoassay (Herrmann et al (*J. Med Virol.* 17:127–33 (1985)) as well. In addition, there was sufficient antigen adsorption of an astrovirus-containing stool suspension to give a positive reaction.

TABLE 1

Reactivity of enteric viruses with monoclonal antibody to astrovirus.

| Virus | Reactivity* | Net $A_{490}$ |
|---|---|---|
| Cell cultivated | | |
| Positive control | + | 1.500 |
| (astrovirus type 2) | | |
| Rotavirus (SA11) | − | 0.001 |
| Calicivirus | − | |
| Feline | − | 0.001 |
| Canine | − | 0.001 |
| Adenovirus | | |
| Type 2 | − | 0.001 |
| Type 40 | − | 0.009 |
| Type 41 | − | 0.001 |
| Coxsackievirus | − | |
| Type A9 | − | 0.013 |
| Type B2 | − | 0.013 |
| Stool derived** | | |
| Astrovirus type 1 | + | 0.345 |
| Norwalk virus | − | 0.001 |
| "Small round virus" | − | 0.015 |
| Hawaii virus | − | 0.015 |
| Calicivirus, human | − | 0.038 |
| Snow Mountain Virus | − | 0.025 |

*Data are positive (+) or negative (−).
**The virus was in 5%–10% stool suspension.

EXAMPLE 5

Antigenic Relationships

The reactivity of rabbit antisera and monoclonal antibody with astrovirus serotypes as determined using the immunofluorescence (IF) technique, described above, is given in Table 2. The rabbit antisera were found to be predominantly type specific, as was originally reported for these sera (Kurtz et al (*Lancet* 2:1405 (1984)). There were some lower-titer, one-way cross-reactions seen between types 1 and 2 antisera and type 5 antigen and between type 4 antisera and type 2 antigen. The monoclonal antibody showed a high titer to all five of the astrovirus serotypes. All types cultivated had been passaged several times—type 1, 20 times; type 2, 30 times; type 4, 10 times; and type 5, 25 times and 26 times. The monoclonal antibody also reacted, by IF, with cultivated Marin County agent after 15 passages in HEK, to a titer of 1:100 000. It was previously demonstrated that Marin County agent is an astrovirus (Herrman et al (*Lancet* 2:743 (1987)). By ELISA (Table 3), the type-specific rabbit antisera were more broadly cross-reactive, especially among types 1, 2 and 5. The monoclonal antibody was reactive with all types.

TABLE 2

Antigenic relationships between astrovirus serotypes, as determined by immunofluorescence.

| Astrovirus serotype* | Reciprocal titer of antibody to serotypes | | | | | |
|---|---|---|---|---|---|---|
| | 1 | 2 | 3 | 4 | 5 | Monoclonal |
| 1 | 1600 | <25 | <25 | <25 | <25 | 100,000 |
| 2 | <25 | 12,800 | <25 | 100 | <25 | 10,000 |
| 3 | 80 | <20 | 320 | <20 | <20 | 20,000 |
| 4 | <25 | <25 | <25 | 3200 | <25 | 100,000 |
| 5 | 50 | 100 | <25 | <25 | 800 | 100,000 |

*Serological data (but not monoclonal antibody data) for serotype 3 are from a previous report (Kurtz et al (Lancet 2:1405 (1984)).

TABLE 3

Antigenic relationships between astrovirus serotypes, as determined by ELISA.

| Astrovirus serotype* | Reciprocal titer of antibody to serotypes | | | | | Monoclonal |
|---|---|---|---|---|---|---|
| | 1 | 2 | 3 | 4 | 5 | |
| 1** | 6400 | 12,800 | <100 | <100 | 400 | <10,000 |
| 2 | 6400 | 6400 | <100 | 800 | 400 | 1,000,000 |
| 3 | NT | NT | NT | NT | NT | 10,000 |
| 4 | 400 | <100 | <100 | 1600 | <100 | 1,000,000 |
| 5 | 6400 | 800 | 400 | 400 | 1600 | 1,000,000 |

*Astrovirus type 3 was used, a seed; there was insufficient material to test all antisera, NT = not tested.
** Plates were coated with rabbit antisera specific towards type 1.

Serotypes of astroviruses were readily distinguishable by using the IF technique. When tested by ELISA, however, there was a high degree of cross-reactivity seen between the astrovirus serotypes; this cross-reactivity indicated the presence of a group antigen. The difference in the specificity seen with IF and ELISA may indicate the manner in which viruses adsorb to solid-phase surfaces. This type of adsorption may result in degradation of the virion and release of group antigenic determinants, as has been reported for coxsackieviruses (Katz et al (*J. Gen. Virol.* 50:357–67 (1980); Hannington et al *J. Med. Microbiol.* 16:459–65 (1983)).

The monoclonal antibodies produced were reactive (by IF, ELISA, or both) with all of the five known astrovirus serotypes and with Marin County agent, an observation that indicates that these viruses share a group antigen.

EXAMPLE 6

Testing of Stool Samples for Astrovirus Specific Antibodies.

Astroviruses types 1–5 and rabbit hyperimmune sera to the five human serotypes were obtained. The methods used for astrovirus cultivation in HEK cells or LLCMK$_2$ cells were as previously described in Example 1. Additional rabbit antiserum was prepared against cell-cultivated astrovirus type 2 for use in ELISA. The virus had been purified by banding in cesium chloride gradients (Lee et al., *J. Hyg. Camb.*) 89:539–540 (1982)), and the virus containing fractions (approximate density 1.36 g/ml were dialyzed against 0.01M phosphate buffered saline, pH 7.0, prior to inoculation. Hybridomas secreting monoclonal antibody to the astrovirus group antigen was prepared as described in Example 1. The stool samples used for detection of astroviruses were diarrheal samples submitted to Central Middlesex Hospital, London, U.K., which had originally been screened by direct EM and were suspected to contain astrovirus particles. These samples were stored at 4° C. for approximately two years prior to testing by immune EM (IEM) and the ELISA reported here. Additional stool samples from pediatric patients negative by ELISA for rotavirus or adenovirus were also tested for astrovirus. The sources of stool samples containing Norwalk virus, calicivirus, Hawaii virus, Snow Mountain virus, and rotaviruses were as previously described. Stools containing adenoviruses were samples from pediatric patients which were found positive by ELISA for adenovirus group antigen or for enteric adenovirus antigen.

Electronmicroscopy (EM) and Immune Electronmicroscopy (IEM)

Fecal samples and cell culture fluids of cultivated viruses were applied to formvar-carbon coated 400 mesh copper grids, stained with 2% phosphotungstic acid in distilled water, and adjusted to a pH 6.4 with 1M potassium hydroxide (KOH). The grids were examined using a Phillips 300 electron microscope for the presence of viral particles. A serum-in-agar technique was used for IEM as described for enteroviruses (Anderson et al., *Canad. J. Microbiol.* 19:585–589 (1973)), using pooled astrovirus types 1–5 rabbit antisera and 2% agarose.

Enzyme Linked Immunoadsorbent Assay

An indirect double antibody assay was used, with monoclonal antibody used as the capture antibody and rabbit antiserum as detector antibody. The antiserum was prepared against astrovirus type 2, but is group-reactive by ELISA. Microtiter plates were coated with monoclonal antibody (as ascitic fluid) to astrovirus group antigen diluted in Vogt's tris-buffered saline to contain approximately 0.5 µg/ml. Antibody was added to microtiter plates (0.10 ml/well) and incubated for 18 hours at 20°–22° C. The antibody solution was removed and the wells post-coated with 1% (w/v) bovine serum albumin (BSA) in 0.01M PBS (pH 7.0) for 18 hours at 4° C. The plates were washed with PBS and stool samples (10% w/v) in PBS were added to the wells (0.10 ml/ml) and incubated for 2 hours at 37° C. The plates were washed 5 times with PBS. Rabbit antiserum to astrovirus was diluted in a solution of 50% fetal calf serum and 50% 0.1M Tris-HCl buffer (pH 7.2) plus 0.15% Tween 20. The diluent also contained 1% goat antiserum to rotavirus, added to block any natural antibody to rotavirus that might be present in the rabbit antiserum. The detector antibody solution (0.05 ml) was added to the wells, incubated for 1.5 hours at 37° C., and the plates washed 5 times. Peroxidase-labelled goat anti-rabbit IgG, heavy and light chains (Kirkegaard and Perry Laboratories, Gaithersburg, Md.), 0.05 ml, at 1 µg/ml in the Tris buffer used above was added and incubated for 1.5 hours at 37° C. The plates were washed 5 times with PBS, soaked for 30 seconds with PBS containing 0.05% Tween-20, and washed again. Substrate for peroxidase was added (O-phenylene-diamine-$H_2O_2$, Abbott Laboratories, North Chicago, Ill.), 0.1 ml, for 10 minutes and the reaction was stopped with 0.2 ml of 1N $H_2SO_4$. The absorbance of the solution was measured at 490 nm in a plate-reader spectrophotometer. Samples were considered positive for astroviruses if the absorbance value was ≧0.1 and ≧3 times the negative control (stool diluent).

EXAMPLE 7

Antigen Detection in Stool Specimens

Stool specimens were tested for the presence of astroviruses by ELISA and compared for sensitivity and specificity to IEM, which was used as the standard test. The results shown in Table 4 demonstrate that the sensitivity was 91% and the specificity, positive and negative predictive values of the ELISA were all ≧94%. The $A_{490}$ values for positive samples ranged from 0.16 to 1.3, with a mean value of 0.61±0.37. The $A_{490}$ values for the two IEM negative, ELISA positive samples were high (1.06 and 0.52), suggesting that viral antigen was present but that intact particles, required for IEM, were either absent or not in sufficient numbers to give a positive IEM result.

TABLE 4

Comparison of Astrovirus ELISA and IEM for the Detection of Astroviruses in Stool Samples of Patients with Gastroenteritis

| Astrovirus Elisa Result | IEM Result Positive | IEM Result Negative | Astrovirus ELISA Sensitivity (%)[a] | Astrovirus ELISA Specificity (%)[b] | PV+ (%)[c] | PV− (%)[d] |
|---|---|---|---|---|---|---|
| Positive | 31 | 2 | 91 | 96 | 94 | 96 |
| Negative | 3 | 54 | | | | |

[a]Sensitivity = ELISA and IEM positives/IEM positives × 100
[b]Specificity = ELISA and IEM negatives/IEM negatives × 100
[c]PV+ = predictive value of a positive test = ELISA and IEM positives/ELISA positives × 100
[d]PV− = predictive value of a negative test = ELISA and IEM negatives/IEM negatives × 100

EXAMPLE 8

Reactivity with Other Viruses in Stools

To determine the selectivity of the astrovirus ELISA, stool specimens containing other viruses were tested. All of the samples were from individual patients and had been shown to contain a specified virus by direct/EM or immunoassay, or by both tests, except for the Hawaii virus samples. The 24 Hawaii virus samples were multiple ones from 9 volunteers who had become ill after receiving a virus suspension, but the stool samples were not assayed for virus content. The results of the selectivity studies are given in Table 5. There were 155 stool samples tested which included 6 virus groups that have been associated with gastroenteritis. The astrovirus ELISA reacted with 3 of the 155, resulting in a false positive reaction rate of 1.9% for these samples. The $A_{490}$ values were 0.61, 0.33, and 0.28; none of the 3 samples could be confirmed as astrovirus positive by IEM. Combined with the astrovirus IEM negative samples shown in Table 4, the overall specificity was 98% (206/211).

TABLE 5

Reactivity of Astrovirus ELISA in Stools Containing Other Viruses

| Virus Identified | No. Tested | Astrovirus ELISA Positive | Astrovirus ELISA Negative |
|---|---|---|---|
| Adenovirus[a] | 30 | 1 | 29 |
| Calicivirus[a] | 70 | 1 | 69 |
| Hawaii virus[b] | 24 | 0 | 24 |
| Norwalk virus[c] | 7 | 0 | 7 |
| Rotavirus[a,c] | 20 | 1 | 19 |
| Snow Mountain virus[c] | 4 | 0 | 4 |

[a]by direct EM
[b]Multiple stool samples from 9 volunteers who became ill. Tests were not done to confirm presence of virus in samples.
[c]by immunoassay

EXAMPLE 9

Astrovirus Group Reactivity

As shown in the previous Examples, the monoclonal antibody to astrovirus was group reactive, and the polyclonal antibody prepared against a specific serotype showed group reactivity by ELISA. The ELISA did not use capture antibody but relied upon non-specific passive adsorption of virus to the microtiter wells, cultivated astrovirus serotype 1 did not appear to be reactive with astrovirus monoclonal antibody, although it was reactive with this antibody in IF tests. To determine if the astrovirus ELISA developed could detect all of the known astrovirus serotypes in stools, representative samples were tested along with culture propagated virus stocks. Virus was identified as to serotype by use of specific rabbit antisera in IEM. The results are shown in Table 6. The ELISA detected all of the serotypes currently known.

TABLE 6

Sensitivity of Astrovirus ELISA for Stools Containing Different Astrovirus Serotypes

| Astrovirus IEM Serotype | No. Stool Samples | Mean $A_{490}$ ± SD | Cell-Grown Virus, $A_{490}$ |
|---|---|---|---|
| 1 | 6 | 0.49 ± 0.29 | 1.01 |
| 2 | 2 | 0.82 ± 0.52 | 1.31 |
| 3 | 1 | 0.72 | 0.51 |
| 4 | 5 | 0.49 ± 0.24 | 0.64 |
| 5 | 2 | 1.389, 0.257[a] | 0.91 |

[a]One sample was diluted 1:10, the second 1:100

The combined use of astrovirus monoclonal and polyclonal antibodies in the ELISA format resulted in an effective method for detection of astrovirus antigen in stool samples obtained from naturally occurring cases of gastroenteritis. The ELISA was found to be comparable in sensitivity to IEM. The specificity for all of the 211 astrovirus IEM negative samples tested was also high (98%). Although mixed monoclonal-polyclonal antibody sandwich-type ELISAs often use the monoclonal antibody as the detector reagent, the sensitivity was higher when the monoclonal antibody was used as the capture antibody. By direct labeling of the monoclonal antibody for use as a detector reagent, the monoclonal antibody can be used for both capture and detector purposes.

Equivalents

Those skilled in the art will know, or be able to ascertain using no more than routine experimentation, many equivalents to the specific embodiments of the invention described herein.

These and all other equivalents are intended to be encompassed by the following claims.

We claim:

1. An immunoassay for detecting the presence or absence of an astrovirus in a biological sample, comprising:
   a) contacting the biological sample with labeled monoclonal antibody produced by hybridoma cell line 8E7 under conditions appropriate for the binding of the monoclonal antibody to the astrovirus group antigen; and
   b) detecting the presence or absence of binding of the labeled monoclonal antibody as an indication of the presence or absence of an astrovirus in the biological sample.

2. An immunoassay according to claim 1 wherein the label is an enzyme, radioisotope, fluorescent compound or particle.

3. An immunoassay for detecting an astrovirus in a biological sample, comprising:
   a) contacting the biological sample with labeled monoclonal antibody produced by the hybridoma cell line 8E7 under conditions which allow the binding of the labeled monoclonal antibody to the group antigen to occur if astrovirus is present in said sample; and
   b) separating the bound labeled monoclonal antibody from the free labeled monoclonal antibody, and c) detecting the bound or free labeled monoclonal antibody as an indication of the amount of an astrovirus in the biological sample.

4. An immunoassay for detecting the presence or absence or quantity of an astrovirus in a sample, comprising:

a) providing a liquid sample to be tested for the presence of the astrovirus;

b) contacting the sample with a first antibody and a second antibody the first antibody being a monoclonal antibody produced by hybridoma cell line 8E7 bound to a solid phase, the second antibody being a labeled polyclonal antibody, under conditions appropriate for the binding of the first and second antibodies to the astrovirus group antigen, the presence or absence or quantity of the astrovirus being determined by measuring either the amount of second antibody bound to the solid phase or the amount of unreacted second antibody.

5. A sandwich immunoassay for detecting the presence or absence of an astrovirus or for quantifying the amount of astrovirus in a sample, comprising:

a) contacting the sample with an immunoadsorbent under conditions which allow the immunoadsorbent to react with a group antigen of astroviruses, the immunoadsorbent being formed by attaching a first antibody reactive with the group antigen of astroviruses to a solid phase, the first antibody being produced by hybridoma cell line 8E7;

b) contacting the product of step (a) with a second antibody which is labeled, the second antibody being polyclonal and reactive with the group antigen of astroviruses under conditions which allow the second labeled antibody to react with the group antigen of astroviruses if astrovirus is present in said sample;

c) separating the free second labeled antibody from the bound second labeled antibody; and d) detecting the label on the bound or free second antibody as an indication of the presence or absence or amount of astroviruses in the sample.

6. A monoclonal antibody produced by hybridoma cell line 8E7.

7. Hybridoma cell line 8E7.

8. A method of diagnosing gastroenteritis in an individual, comprising:

a) contacting a biological sample from the individual with a labeled monoclonal antibody produced by hybridoma cell line 8E7; and b) detecting specific binding of the label as an indication of the presence or absence of gastroenteritis.

9. A kit for detecting the presence or absence or amount of astrovirus in a biological sample comprising, a container comprising a labeled monoclonal antibody produced by hybridoma cell line 8E7.

10. A kit for detecting the presence or absence or amount of astrovirus in a biological sample, comprising:

a) a solid phase having a first antibody reactive with the group antigen of astroviruses adsorbed thereon, the first antibody being a monoclonal antibody produced by hybridoma cell line 8E7; and b) a container comprising a second antibody reactive with the group antigen of astroviruses, the second antibody being a polyclonal antibody.

11. An immunoassay for detecting astrovirus in a sample, comprising the steps of:

a) providing an immunoadsorbent comprising polyclonal antibodies reactive with astrovirus group antigen, fixed to a solid support;

b) contacting the sample with the immunoadsorbent under conditions appropriate for the binding of astrovirus in the sample to the polyclonal antibodies;

c) washing the immunoadsorbent to remove non-specifically bound material;

e) contacting the immunoadsorbent from step c) with a solution containing monoclonal antibodies produced by hybridoma cell line 8E7;

f) detecting specific binding of the monoclonal antibodies to the immunoadsorbent as an indication of the presence of astrovirus in the sample.

* * * * *